United States Patent
Kumar et al.

(10) Patent No.: US 9,910,025 B2
(45) Date of Patent: Mar. 6, 2018

(54) INTEGRATED ACTIVE FUEL CHARACTERISTIC SENSOR

(71) Applicant: Simmonds Precision Products, Inc., Vergennes, VT (US)

(72) Inventors: Lalit Al Kumar, Shelburne, VT (US); Rollin W. Brown, South Burlington, VT (US); Richard T. Williams, Pittsford, VT (US); Peter Simonds Gras, Jr., Charlotte, VT (US)

(73) Assignee: Simmonds Precision Products, Inc., Vergennes, VT (US)

( * ) Notice: Subject to any disclaimer, the term of this patent is extended or adjusted under 35 U.S.C. 154(b) by 129 days.

(21) Appl. No.: 14/746,971

(22) Filed: Jun. 23, 2015

(65) Prior Publication Data

US 2016/0377587 A1    Dec. 29, 2016

(51) Int. Cl.
```
G01N 33/22      (2006.01)
G01F 23/292     (2006.01)
G01F 23/26      (2006.01)
G01N 29/024     (2006.01)
G01N 9/00       (2006.01)
G01N 25/00      (2006.01)
B64D 37/00      (2006.01)
G01N 27/22      (2006.01)
```
(Continued)

(52) U.S. Cl.
CPC ............ *G01N 33/22* (2013.01); *B64D 37/005* (2013.01); *G01F 23/0076* (2013.01); *G01F 23/0092* (2013.01); *G01F 23/26* (2013.01); *G01F 23/263* (2013.01); *G01F 23/292* (2013.01); *G01F 23/2921* (2013.01); *G01N 9/00* (2013.01); *G01N 25/00* (2013.01); *G01N 27/221* (2013.01); *G01N 29/024* (2013.01); *B60K 2015/03223* (2013.01); *G01N 2291/02818* (2013.01)

(58) Field of Classification Search
CPC .......... G01N 33/22; G01N 9/00; G01N 25/00; G01N 29/024; G01N 27/221; G01N 2291/02818; G01F 23/26; G01F 23/292; G01F 23/0076; G01F 23/0092; G01F 23/263; G01F 23/2921; B64D 37/005; B60K 2015/03223
USPC ................................. 73/32 A, 304 R, 304 C
See application file for complete search history.

(56) References Cited

U.S. PATENT DOCUMENTS

| | | | | |
|---|---|---|---|---|
| 4,745,293 A | * | 5/1988 | Christensen | ........ G01F 23/292 250/227.23 |
| 5,187,979 A | * | 2/1993 | Edmark, III | ........ G01F 23/263 141/115 |

(Continued)

FOREIGN PATENT DOCUMENTS

KR    2016069563 A  *  6/2016  ........... G01F 23/296

OTHER PUBLICATIONS

European Search Report for European Application No. 16175733.1 dated Dec. 21, 2017.

*Primary Examiner* — Hezron E Williams
*Assistant Examiner* — Marrit Eyassu
(74) *Attorney, Agent, or Firm* — Carlson, Gaskey & Olds, P.C.

(57) ABSTRACT

An aircraft fuel system comprises an integrated sensor assembly incorporating a housing. The housing receives a circuit board, a temperature sensor, a point level sensor and a fuel density sensor. A first fuel height sensor is positioned outwardly of the housing.

14 Claims, 3 Drawing Sheets

(51) Int. Cl.
*G01F 23/00* (2006.01)
*B60K 15/03* (2006.01)

(56) References Cited

U.S. PATENT DOCUMENTS

| | | | | |
|---|---|---|---|---|
| 5,189,911 | A * | 3/1993 | Ray | G01F 23/2963 324/207.13 |
| 5,265,460 | A * | 11/1993 | Ellinger | G01N 9/00 73/32 R |
| 5,880,480 | A | 3/1999 | Ellinger et al. | |
| 6,577,960 | B1 | 6/2003 | Rabelo et al. | |
| 7,581,434 | B1 | 9/2009 | Discenzo et al. | |
| 7,775,092 | B2 | 8/2010 | Murphy et al. | |
| 8,191,419 | B2 | 6/2012 | Wilby | |
| 8,281,655 | B2 * | 10/2012 | Bahorich | G01F 23/266 73/304 C |
| 2004/0074294 | A1 * | 4/2004 | Boucher | G01C 13/008 73/187 |
| 2005/0262953 | A1 * | 12/2005 | Pooley | G01R 1/06788 73/866.5 |
| 2007/0113625 | A1 * | 5/2007 | Sasanuma | F01N 3/2066 73/61.46 |
| 2009/0234597 | A1 * | 9/2009 | Wilby | G01F 23/268 702/55 |
| 2010/0251816 | A1 | 10/2010 | Bahorich et al. | |
| 2012/0118059 | A1 * | 5/2012 | Reimer | F01N 3/2066 73/290 V |
| 2012/0251147 | A1 * | 10/2012 | Gomi | G03G 15/105 399/58 |
| 2014/0083182 | A1 * | 3/2014 | Cantolino | G01F 23/00 73/290 R |
| 2015/0000396 | A1 * | 1/2015 | Maguin | F01N 3/2066 73/290 V |
| 2015/0022376 | A1 | 1/2015 | Zhang et al. | |
| 2016/0041024 | A1 * | 2/2016 | Reimer | G01F 23/2962 73/290 V |

* cited by examiner

INTEGRATED ACTIVE FUEL CHARACTERISTIC SENSOR

BACKGROUND

Sensors for sensing characteristics of fuel on high technology systems, such as aircraft, are becoming increasingly complex. As an example, it is known to have fuel height sensors, fuel dielectric sensors, temperature sensors, point level sensors to provide a level warning (such as low or high), and ultrasonic sensors to measure a density of fuel.

In the prior art, these sensors were all mounted individually and electrical connections (wires) had to extend between them and the interface electronics to communicate appropriate signals.

SUMMARY

An aircraft fuel measurement system comprises an integrated sensor assembly incorporating a housing. The housing receives a circuit board, a temperature sensor, a point level sensor and a fuel density sensor. A first fuel height sensor is positioned outwardly of the housing.

These and other features may be best understood from the following drawings and specification.

DETAILED DESCRIPTION

Figure 1:
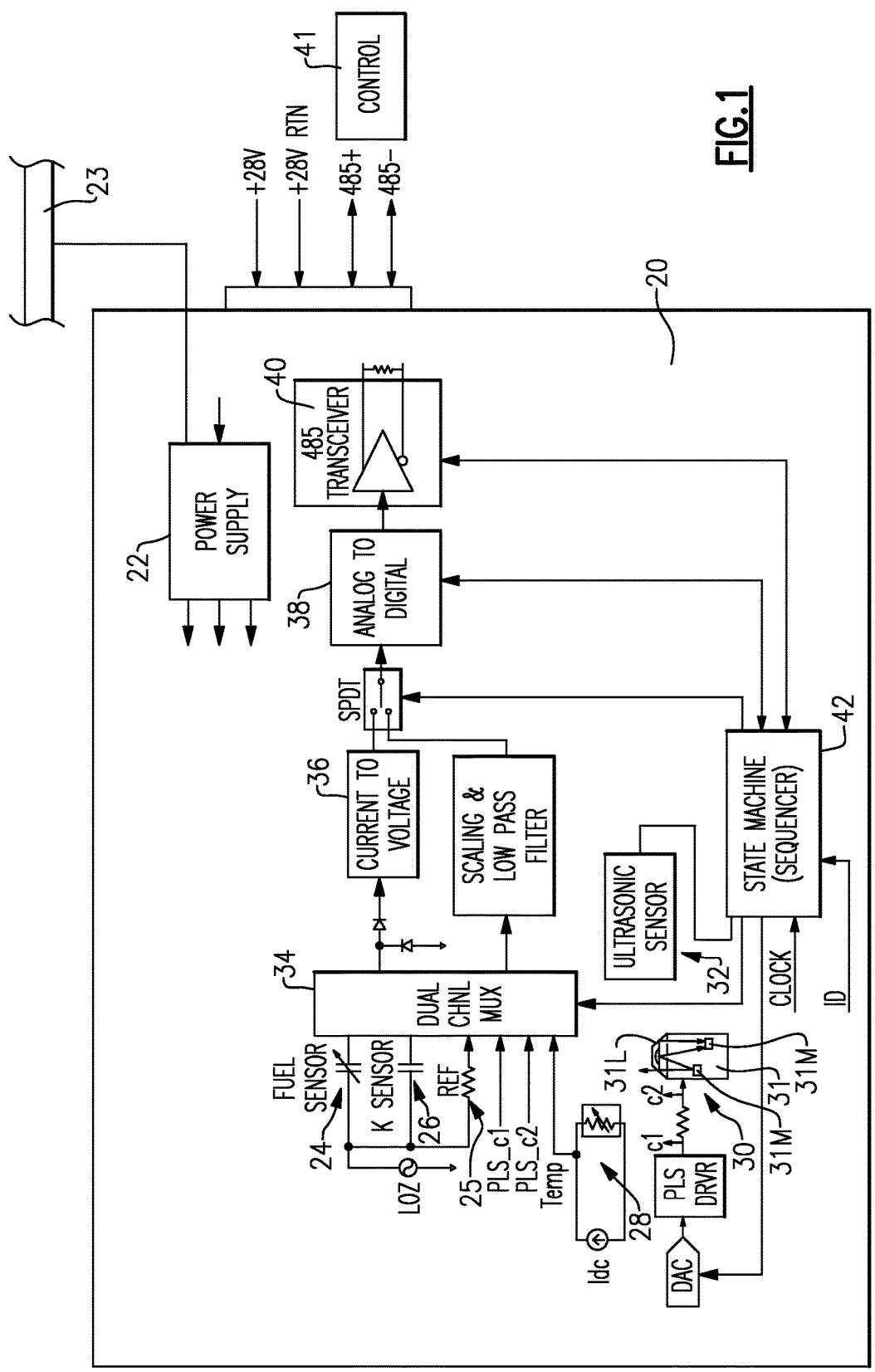
FIG. 1 is a schematic of a combined fuel characteristic sensor.

FIG. 1 is a schematic of an integrated fuel characteristic sensor 20. A power supply 22 supplies power. A fuel height sensor 24 is included. A dielectric (K) sensor (a compensator) 26 is also included and measures fuel dielectric. The fuel height sensor 24 consists of a low voltage (e.g., 5 five volts RMS nominal), AC excitation signal generator (e.g., 5 to 20 KHz nominal range) along with a current-to-voltage converter. An excitation signal is generated under the control of a sequencer 42 and connected to the fuel sensor. The excitation signal is rectified and returned as a current signal proportional to the fuel height. A current-to-voltage converter 36 converts and scales the signal accordingly. The signal is applied to an analog-to-digital converter 38 and input into a transceiver 40. The transceiver communicates over a serial data bus with a control 41. While the connection is disclosed as hard wired, wireless communication systems may be used. The dielectric sensor may be eliminated in some embodiments.

Control 41 may be a control for an associated gas turbine engine, or may be a standalone control. Control 41 takes in signals from one or more sensors and utilizes those signals to provide information with regard to the fuel, such as determine fuel mass or to control an associated fuel pump or an associated gas turbine engine.

A reference signal (REF) 25 is created and driven by the same excitation signal as the fuel height sensor 24 to remove electronic errors associated with gain and offsets and other associated errors.

The dielectric sensor 26 is designed into the electronics and its functionality is the same as the fuel height sensor 24. The dielectric sensor 26 when used, however, utilizes a fixed capacitance to determine fuel dielectric whereas the capacitance of a fuel height sensor 24 is variable, dependent on the portion immersed in fluid.

A sampling approach ensures an assessment of the health of the individual sensors. That is, by having redundant sensors 24 and 26, the health of each sensor can be checked by comparing the determined signals. The excitation signal is sampled at the signal conditioner as a check on a source signal. An out of range signal received by the control 41 indicates a failure of one of the signals.

The power supply 22 provides the voltages required by the circuitry and may be for example, 28 volts DC from an aircraft's power bus 23, shown schematically, or other suitable source scaled for the housing electronics. It may be current limited (e.g., 100 milliamps) via a resistive element which becomes open circuit should the current exceed a specified limit to maintain safe operation of the sensor. The power supply circuitry may utilize step-down DC/DC regulators when available, which may be off the shelf items. The power supply is protected against electromagnetic interference (radio frequency interference for example) and voltage transients (lightning for example).

An optical point level sensor 30 is utilized as an independent fuel warning indication, low or high for example. The optical point level sensor 30 is operable to determine whether a fuel height is above or below a predetermined level. As illustrated in FIG. 1, a cone 31 includes an LED 31L. The LED 31L bounces a light off a pair of minors 31M, and outwardly of a cone 31. As will be explained below, this light allows the sensor 30 to determine whether the fuel level is above or below a predetermined amount.

The optical sensor operates in three modes. Two of the modes are built in test functions. Each mode is activated by sensor electronics sending a specific voltage level to the sensor. The operational mode is activated by the receipt of a signal (e.g., four volts) by the sensor and a return signal indicating a wet or dry condition. The first built-in test (BIT) function is activated by the receipt of a six volt signal which verifies the health of the optical components in an active state. Stated another way, the LED 31L is activated (illuminated) and a photo darlington detector is activated by the light received from the LED 31L. A second BIT function is activated by the receipt of a voltage signal (e.g., eight volt) from the sensor electronics which verifies the health of the optical components in an inactive state. The LED 31L is deactivated, at which point, the photodetectors should not receive any light or be activated.

A fuel temperature sensor 28 is used to measure fuel temperature. The sensor may be a resistive element whose value changes when the fuel temperature varies. An independent DC current source (e.g., approximately 2 milliamps) provides an excitation signal to the sensor. The return signal is a voltage which is then digitized and from this information the fuel temperature is computed.

Figure 2:
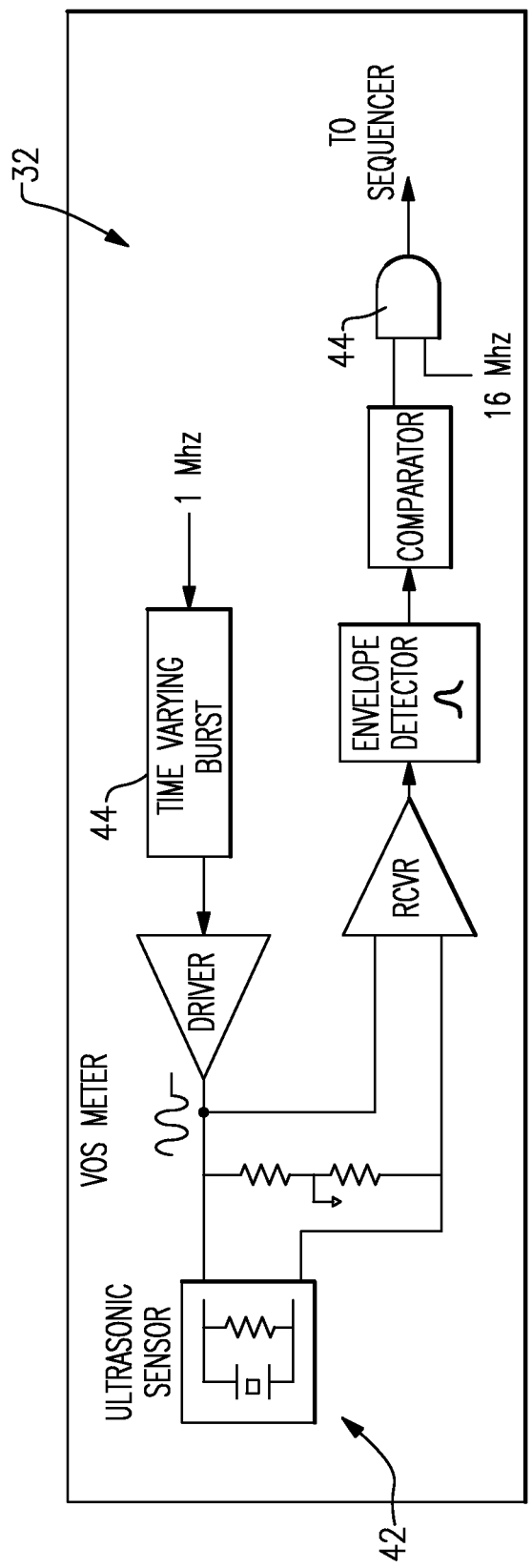
FIG. 2 shows a sub-circuit within the FIG. 1 integrated sensor.

A fuel density sensor includes an ultrasonic sensor 32 provides a measurement signal from which density can be computed. Notably, the ultrasonic sensor 32 may be eliminated in some embodiments. The determination of fuel density utilizes information from the ultrasonic sensor 32, the fuel temperature measurement sensor 28, and fuel dielectric sensor 26. The circuit 32 is shown in further detail in FIG. 2. The velocity of sound must be determined when immersed in the fuel. The velocity of sound is determined by utilizing the ultrasonic density sensor 32 and a fixed target. The sensor is excited by a sinusoidal burst at some frequency (e.g., 1 MHz). A sound wave travels from the sensor surface to its target and back. The time of flight is measured under the control of sequencer 42 (See FIG. 1).

From the determined flight time, the velocity of sound in the fuel is calculated. By measuring the velocity of sound, dielectric constant and temperature, a fuel density may be inferred.

The ultrasonic method of measuring fuel density offers substantial cost savings when compared to alternatives.

Notably, the operation of the sensors 24, 26, 28, 30, and 32 are all generally as known. It is the inclusion of all of these sensors into a single integrated sensor assembly which is unique to this disclosure. The incorporation of all of the sensors eliminates external wires. As will be explained below, the sensors are all connected directly into an integrated circuit board positioned within a housing. The sensors, and their interconnection, are all better protected than the separate sensors of the prior art. The integrated sensor assembly 20 is thus more resistant to environmental challenges within the field.

Figure 3A:
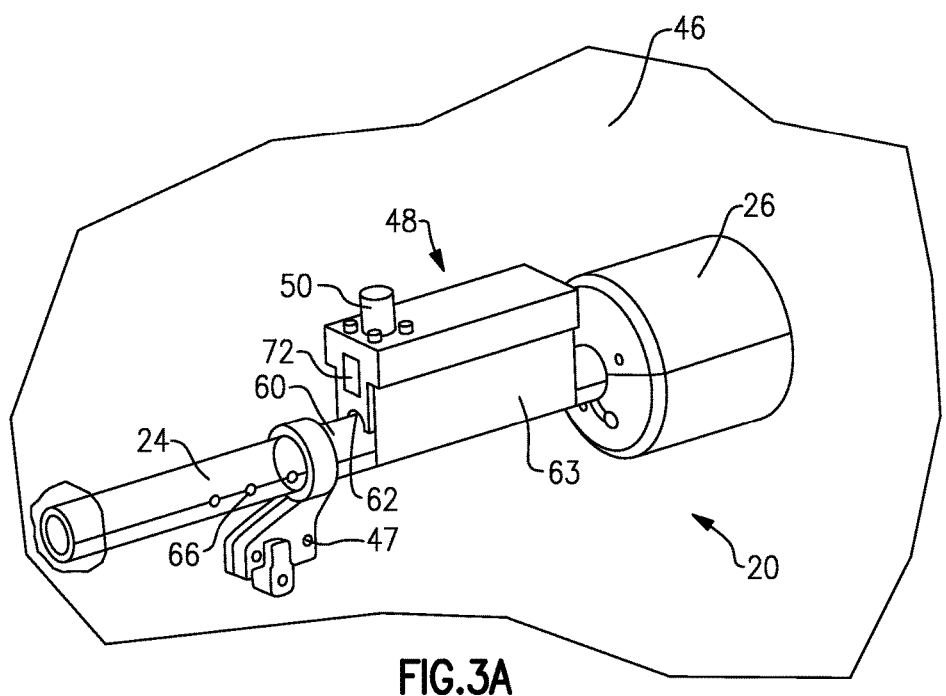
FIG. 3A is a first perspective view of the integrated sensors.

FIG. 3A shows the combined sensor 20. A fuel tank 46 is shown around the sensor 20. The fuel height sensor 24 is shown with circuitry box 48 and fuel dielectric sensor 26 as an assembly.

Circuitry box or housing 48 receives a connector 50 for receiving the power and communication data with a terminal block cover 52. A circuit board 51 is positioned within the housing wall 54. The temperature sensor 28 is positioned on an opposed side of the circuit board 51 from the connector 50. The fuel density sensor 32 is shown adjacent to the temperature sensor 28. The optical point level sensor 30 is shown adjacent to a forward end of the housing wall 54. The fuel density sensor 32 is shown schematically housing a sound wave off a surface 56, which may be a part of a fuel tank.

Stated in one way, an integrated sensor assembly 20 for use on an aircraft fuel system has a housing 48 which receives a circuit board 51, a temperature sensor 28, and an optical point level sensor 30 and a fuel density sensor 32. A fuel height sensor 24 is positioned outwardly of the housing 48.

Figure 3B:
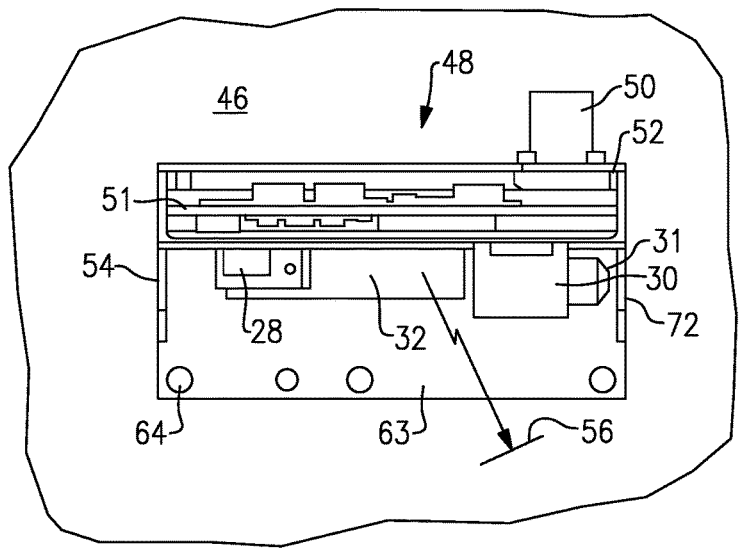
FIG. 3B is a cross-sectional view through a portion of the integrated sensors.
Figure 3C:
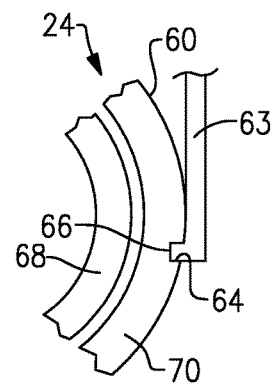
FIG. 3C shows another detail.

The unique packaging can be best understood from FIGS. 3A, 3B, and 3C. As shown in FIG. 3A, the fuel height sensor 24 essentially is an elongate tubular or cylindrical member. The fuel dielectric sensor 26 is attached to the tube structure of the fuel height sensor 24. The circuitry box 48 sits adjacent to the fuel dielectric sensor 26, and on an outer surface 60 of the fuel height sensor. As shown, the fuel height sensor outer surface 60 is generally cylindrical, and the circuitry box 48 has a part cylindrical portion 62, which sits on the cylindrical outer surface 60. A flat plate 63 is also formed as part of the circuitry box 48. As shown in FIG. 3A, there are a number of depressions 66 in the outer surface 60. Similar depressions are obscured in this view by flat plate 63. As shown in FIG. 3B, there are a number of tabs 64 facing inwardly of the flat surface 63.

As can be appreciated from FIGS. 3A and 3B, a lens 72 is positioned within the circuitry housing 48. The lens 72 can be seen in FIG. 3B to be positioned outwardly of the cone 31. The light from cone 31 reflects outwardly as shown schematically in FIG. 1, moves through the lens 72, and, by the reflected signal, sensor 30 can determine whether that signal is sent outwardly into fuel, or whether it is above a fuel level. In this manner, whether the fuel level is above or below a predetermined level can be determined.

As can be appreciated from FIG. 3C, the tabs 64 snap into the depressions 66 in an outer surface 60 of the fuel height sensor 24 to secure the housing on the cylindrical outer surface. As shown in FIG. 3C, as known, the fuel height sensor 24 has a pair of coaxially extending cylindrical or tubular portions 68 and 70.

A bracket 47 serves to attach the integrated sensor assembly 20 to the fuel tank 46. In practice, more than one bracket 47 may be utilized.

Fuel height sensor 24 includes a pair of coaxial tubular members 68 and 70, and an outer surface 60. The circuitry housing 48 is mounted on the outer surface 60. An outer one 70 of the tubular members defining a cylindrical outer surface. The housing 48 has a part cylindrical portion 62 received on the cylindrical outer surface.

Figure 3D:
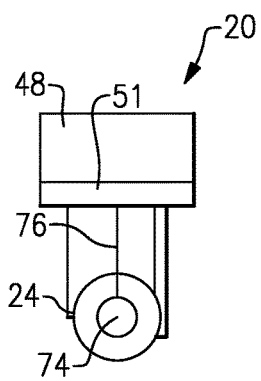
FIG. 3D shows another detail.

FIG. 3D shows electronics 74 which are part of the fuel height sensors 24 and 26. A wire 76 is shown extending from electronics 74, into the circuitry housing 48, and connecting into the circuit board 51. Although shown schematically, a worker of ordinary skill in the art would understand how to communicate sensors 24 and 26 to the circuit board 51.

It should also be understood, all of the other sensors that are positioned within the housing 48 also communicate through the single circuit board 51. Thus, another beneficial feature of the integrated sensor assembly 20 is that a single circuit board communicates and processes the signals from each of the several sensors.

In one embodiment, the circuitry housing 48 is formed of a nylon material.

By integrating all of the sensors within an integrated sensor 20, all of the extending wires required by the prior separate sensors are eliminated.

Although an embodiment of this invention has been disclosed, a worker of ordinary skill in this art would recognize that certain modifications would come within the scope of this invention. For that reason, the following claims should be studied to determine the true scope and content of this invention.

The invention claimed is:

1. An integrated sensor assembly for use on an aircraft fuel system comprising:
   the integrated sensor assembly incorporating a housing, said housing receiving a circuit board, a temperature sensor, a point level sensor and a fuel density sensor;
   a first fuel height sensor positioned outside of said housing;
   wherein there is a second fuel height sensor, and said second fuel height sensor determines a dielectric constant of the fuel and utilizes it to determine fuel height;
   wherein said second fuel height sensor is also positioned outside of said housing;
   wherein said first fuel height sensor includes a pair of coaxial tubular members having an outer surface, with an outer one of said tubular member having a cylindrical outer surface, and said housing having a part cylindrical portion received on said cylindrical outer surface; and
   wherein said housing also having a flat plate, and there being tabs on one of said cylindrical outer surface and an inner surface of said flat plate, and there being depressions in the other of said cylindrical outer surface and said inner surface with said tabs being received within said depressions to secure said housing on said cylindrical outer surface.

2. The integrated sensor assembly as set forth in claim 1, wherein said first fuel height sensor utilizes a variable capacitance to determine fluid height.

3. The integrated sensor assembly as set forth in claim 2, wherein said second fuel height sensor utilizes a fixed capacitance.

4. The integrated sensor assembly as set forth in claim 2, wherein said fuel density sensor receives signals relative to the dielectric constant, and from the fuel temperature sensor, the fuel density sensor includes an ultrasonic sensor that creates a sound wave which travels from a sensor surface to a target and back through the fuel, and a time of travel is measured, and from the time of travel, a velocity of sound in fuel is calculated, and fuel density is determined.

5. The integrated sensor assembly as set forth in claim 2, wherein said point level sensor includes a light source to determine if a fuel level is below a predetermined level.

6. The integrated sensor assembly as set forth in claim 5, wherein said point level sensor has test functions to determine whether said point level sensor is operating properly.

7. The integrated sensor assembly as set forth in claim 1, wherein said fuel density sensor receives signals relative to the determined dielectric constant and from the fuel temperature sensor, the fuel density sensor includes an ultrasonic sensor that creates a sound wave which travels from a sensor surface to a target and back through the fuel, and a time of travel is measured, and from the time of travel, a velocity of sound in fuel is calculated, and fuel density is determined.

8. The integrated sensor assembly as set forth in claim 1, wherein at least one wire extends from said first fuel height sensor into said housing.

9. The integrated sensor assembly as set forth in claim 8, wherein said at least one wire from said first fuel height sensor is connected into said circuit board.

10. The integrated sensor assembly as set forth in claim 9, wherein said temperature sensor, said point level sensor, and said fuel density sensor also communicate to said circuit board.

11. The integrated sensor assembly as set forth in claim 1, wherein said fuel density sensor receives signals relative to a determined dielectric constant, and from the fuel temperature sensor, the fuel density sensor includes an ultrasonic sensor that creates a sound wave which travels from a sensor surface to a target and back through the fuel, and a time of travel is measured, and from the time of travel, a velocity of sound in fuel is calculated, and fuel density is determined.

12. The integrated sensor assembly as set forth in claim 1, wherein said point level sensor includes a light source to determine if a fuel level is below a predetermined level.

13. The integrated sensor assembly as set forth in claim 12, wherein said light source sends a light signal through a lens positioned within said housing to determine whether said fuel level is below said predetermined level.

14. An integrated sensor assembly for use on an aircraft fuel system comprising:
  a housing, said housing receiving a circuit board, a temperature sensor, an optical point level sensor, and a fuel density sensor that receives signals relative to a dielectric constant, and from the temperature sensor, the fuel density sensor includes an ultrasonic sensor that creates a sound wave which travels from a sensor surface to a target and back through the fuel, and a time of travel is measured, and from the time of travel, a velocity of sound in fuel is calculated, and fuel density is determined;
  a first fuel height sensor positioned outside of said housing, said first fuel height sensor includes a pair of coaxial tubular members having an outer surface, with an outer one of said tubular members having a cylindrical outer surface, and said housing having a part cylindrical portion received on said cylindrical outer surface;
  a second fuel height sensor is included, and is positioned outside of said housing and determines said dielectric constant of the fuel and to further utilize it to determine fuel height;
  said housing having a flat plate, and there being tabs on one of said cylindrical outer surface and an inner surface of said flat plate, and there being depressions in the other of said cylindrical outer surface and said flat plate, with said tabs being received within said depressions to secure said housing on said cylindrical outer surface; and
  at least one wire extending from said fuel height sensor into said housing; said circuit board being positioned within said housing and said at least one wire from said first fuel height sensor being connected into said circuit board, and said temperature sensor, said optical point level sensor, and said fuel density sensor also communicating to said circuit board.

* * * * *